(12) United States Patent
Hayes et al.

(10) Patent No.: US 7,144,399 B2
(45) Date of Patent: Dec. 5, 2006

(54) INSTRUMENTATION GUIDE FOR ORTHOPEDIC SURGERY

(75) Inventors: Kiele S Hayes, Philadelphia, PA (US); James T Brumley, Littleton, CO (US)

(73) Assignee: Zimmer Technology, Inc., Chicago, IL (US)

( * ) Notice: Subject to any disclaimer, the term of this patent is extended or adjusted under 35 U.S.C. 154(b) by 405 days.

(21) Appl. No.: 10/280,838

(22) Filed: Oct. 25, 2002

(65) Prior Publication Data
US 2004/0082959 A1  Apr. 29, 2004

(51) Int. Cl.
*A61B 17/17* (2006.01)
(52) U.S. Cl. .......................................... 606/98; 606/96
(58) Field of Classification Search ............ 606/86–89, 606/96–98
See application file for complete search history.

(56) References Cited

U.S. PATENT DOCUMENTS

| | | | |
|---|---|---|---|
| 4,570,624 A | 2/1986 | Wu ........................ 128/92 EB |
| 4,622,959 A | 11/1986 | Marcus ................... 128/92 YZ |
| 4,805,607 A | 2/1989 | Engelhardt et al. ..... 128/92 YZ |
| 4,881,535 A | 11/1989 | Sohngen ....................... 606/98 |
| 4,911,153 A | 3/1990 | Border ......................... 606/98 |
| 4,969,889 A | 11/1990 | Greig .......................... 606/97 |
| 4,978,351 A | 12/1990 | Rozas .......................... 606/98 |
| 5,100,404 A * | 3/1992 | Hayes ......................... 606/62 |
| 5,178,621 A * | 1/1993 | Cook et al. ................... 606/96 |
| 5,334,205 A * | 8/1994 | Cain ........................... 606/96 |
| 5,478,341 A | 12/1995 | Cook et al. ................... 606/62 |
| 5,514,139 A | 5/1996 | Goldstein et al. |
| 5,597,379 A | 1/1997 | Haines et al. |
| 5,643,272 A | 7/1997 | Haines et al. |
| 5,688,271 A * | 11/1997 | Faccioli et al. ............... 606/54 |
| 5,755,803 A | 5/1998 | Haines et al. |
| 5,810,827 A | 9/1998 | Haines et al. |
| 5,879,354 A | 3/1999 | Haines et al. |
| 6,056,754 A | 5/2000 | Haines et al. |
| 6,197,064 B1 | 3/2001 | Haines et al. |
| 6,695,848 B1 | 2/2004 | Haines et al. |

FOREIGN PATENT DOCUMENTS

GB      2230453 A   * 10/1990

* cited by examiner

*Primary Examiner*—Eduardo C. Robert
*Assistant Examiner*—D. Jacob Davis
(74) *Attorney, Agent, or Firm*—Baker & Daniels LLP

(57) ABSTRACT

An instrumentation guide for orthopedic surgery having guide body includes at least one alignment guide. An attachment member is securable to the guide body and provides for the attachment of an orthopedic device such as an intramedullary nail. A transfer member which can be both engaged and disengaged with the instrumentation guide while a nail is secured to the attachment member is used to transmit insertion and removal forces to the nail through the attachment member. The transfer member may be formed out of a metal material and be removed from the guide body, which may be substantially radio transparent, while the nail is still attached to the guide body to facilitate the acquisition of radiographic images. The transfer member include an inner shaft and an outer sleeve which are relatively rotatable. The transfer member may also include a quick connect mechanism.

20 Claims, 4 Drawing Sheets

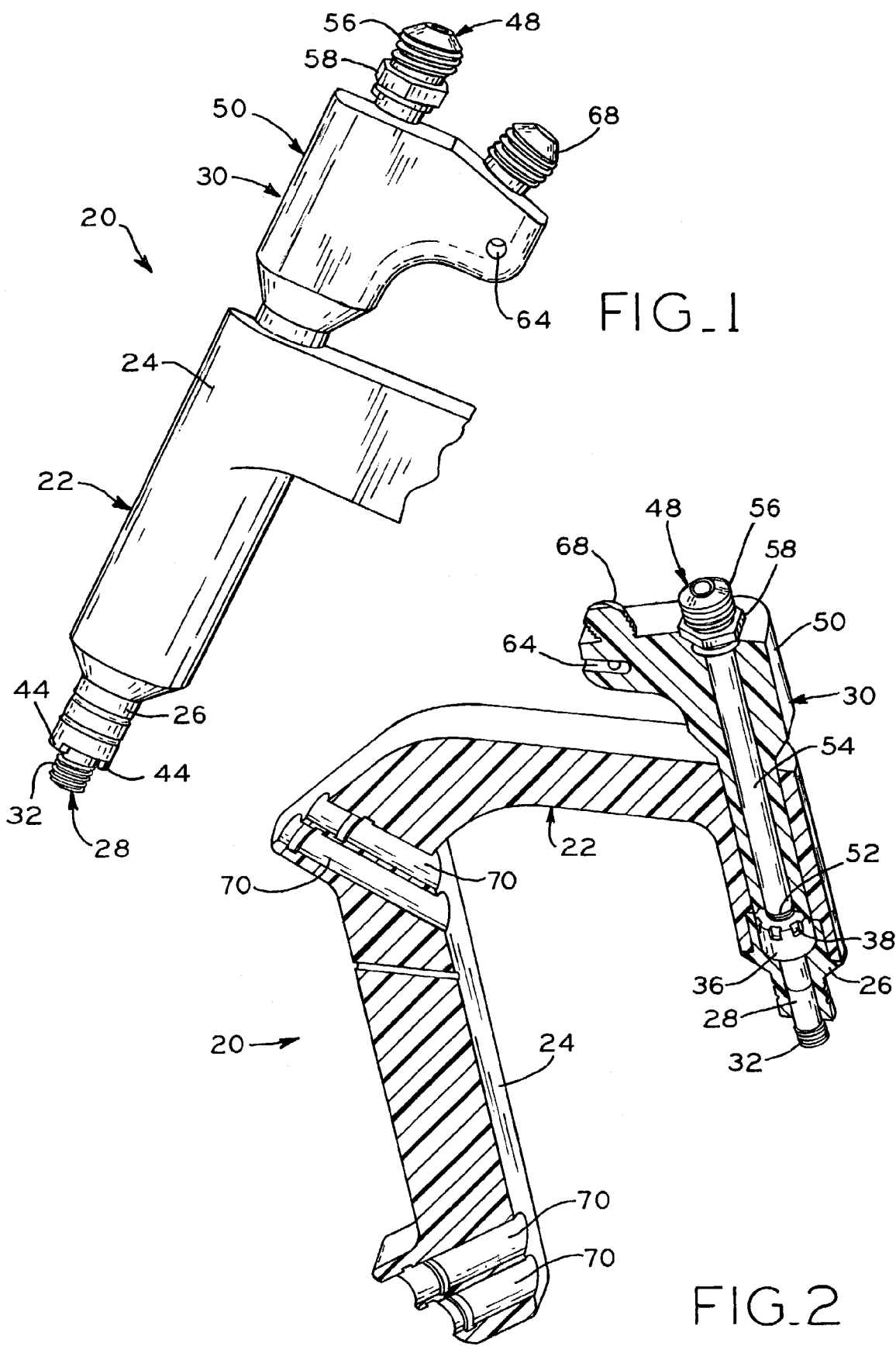
FIG_1
FIG_2

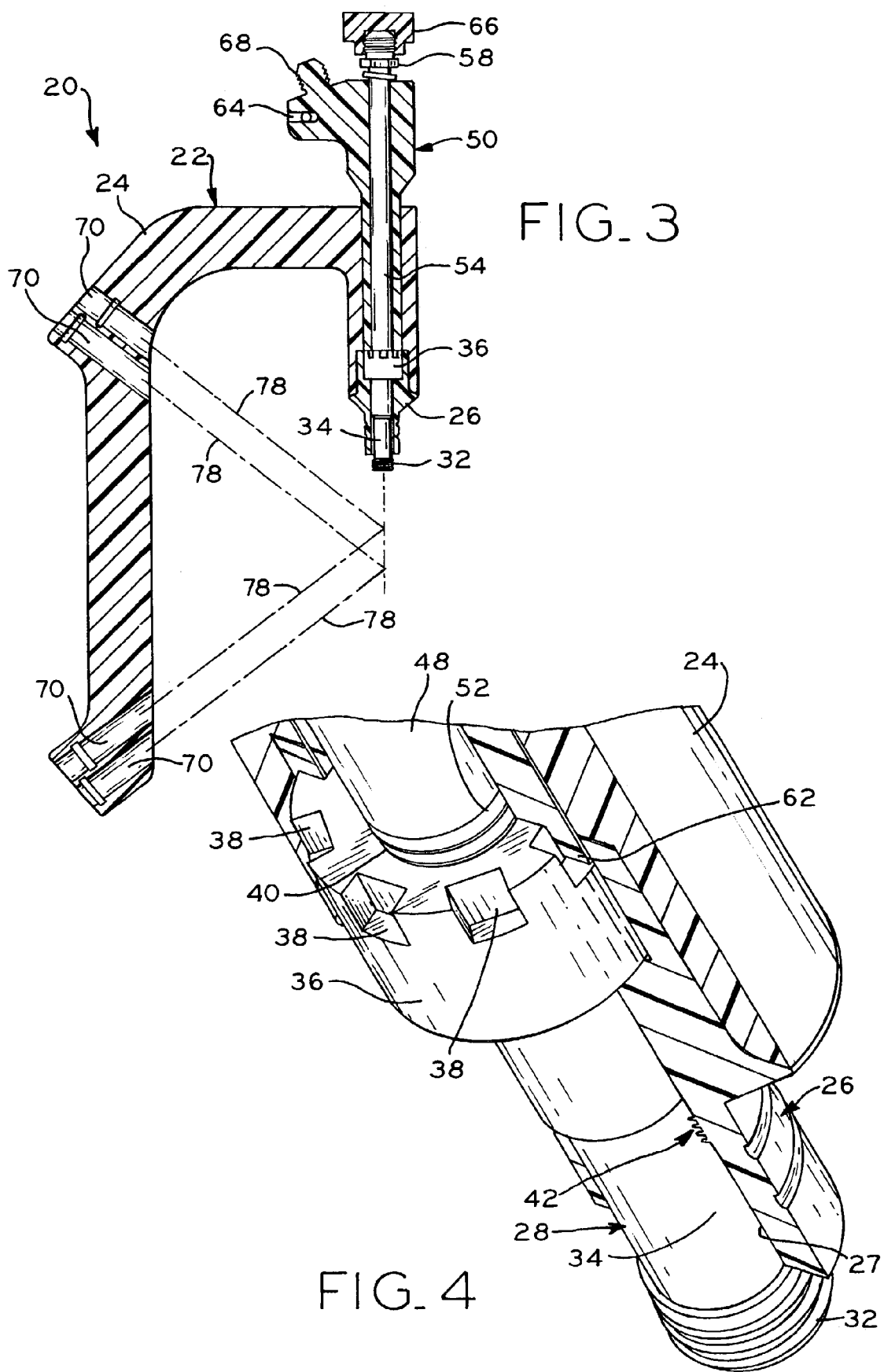

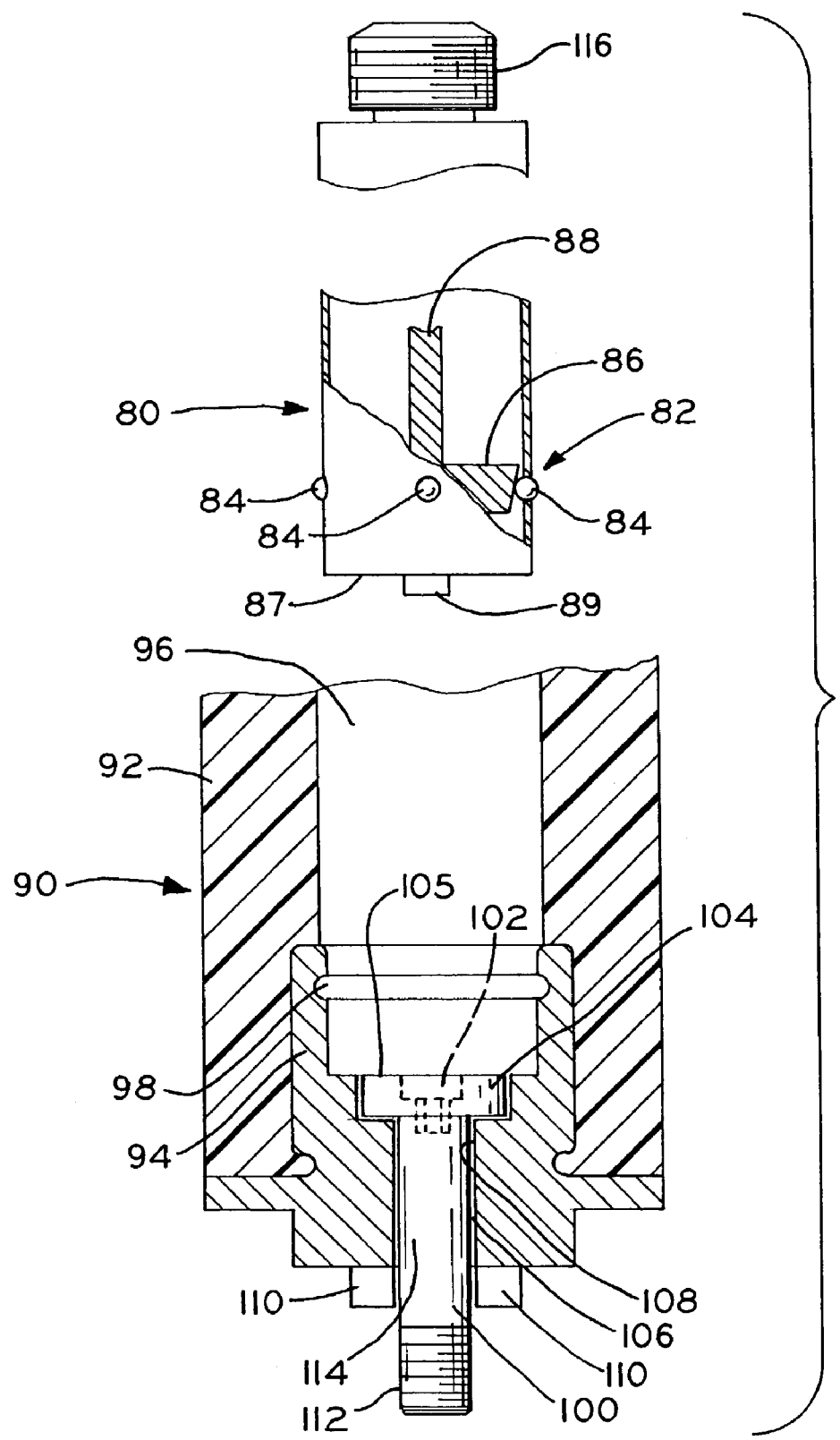
FIG_7

INSTRUMENTATION GUIDE FOR ORTHOPEDIC SURGERY

BACKGROUND OF THE INVENTION

The present invention relates to an instrumentation guide which can be used in orthopedic surgery. The instrumentation guide of the present invention may be used with intramedullary nails or rods.

Intramedullary nails are often used by orthopedic surgeons to secure a fracture of a long bone such as a femur. After the nail has been inserted into the intramedullary canal of the fractured bone, screws may be inserted through the bone and nail at an angle to the longitudinal axis of the nail. An instrumentation guide, or targeting device, is typically used to align the screws with openings in the nail. The instrumentation guide is generally secured to one end of the nail to fix the position of the nail with respect to the body of the instrumentation guide which is then used to align the drill and screws. It is also typical to obtain radiographic images during the procedure to ensure the proper alignment of the screws prior to drilling through the bone.

SUMMARY OF THE INVENTION

The present invention provides an improved instrumentation guide for use with an orthopedic device such as an intramedullary nail or rod and the instruments associated therewith.

The invention comprises, in one form thereof, an instrumentation guide having a guide body which defines a cavity and includes at least one alignment feature. An attachment member is secured to the guide body. An orthopedic device is attachable to the attachment member in a predetermined position relative to the instrumentation guide. A transfer member having first and second ends is also provided. The first end of the transfer member is insertable into the guide body cavity. The transfer member is engageable with the instrumentation guide to secure the transfer member in a fixed position relative to the attachment member. The transfer member is both engageable and disengagable with the instrumentation guide while the orthopedic device is attached to the attachment member. The second end of the transfer member includes a force receiving member which is positioned outside the guide body cavity when the first end of the transfer member is engaged with the instrumentation guide.

The attachment member may include first and second portions wherein the orthopedic device is attachable to the first portion and the second portion is disposed in the guide body cavity. The transfer member can be secured in a fixed position by engagement of the first end of the transfer member with the second portion of the attachment member.

The guide body of the instrumentation guide may be substantially radio-transparent and may have two portions, a first guide body portion being radio-transparent and the second guide body portion being metallic wherein the attachment member is securable to the second guide body portion. The transfer member may comprise first and second members which are relatively rotatable and wherein the first member is an inner shaft and the second member is an outer sleeve.

The invention comprises, in another form thereof, an instrumentation guide having a guide body with at least one alignment feature. An attachment member is secured to the guide body and an orthopedic device is attachable to the attachment member in a predetermined position relative to the instrumentation guide. A transfer member assemblage having first and second ends is also provided. The first end of the transfer member assemblage is both engageable and disengagable with the instrumentation guide while the orthopedic device is attached to the attachment member. The transfer member assemblage includes relatively rotatable first and second transfer members, wherein engagement of the first end of the transfer member assemblage with the instrumentation guide comprises relative rotation between the first and second transfer members. A force receiving member is disposed on the transfer member assemblage proximate the second end of the assemblage.

The transfer member assemblage may have a first transfer member which includes an elongate shaft and the second transfer member may be an outer sleeve wherein the force receiving member is disposed on the first transfer member.

The transfer member assemblage may also take the form of a first transfer member which comprises an elongate shaft having a threaded end which is engageable with the attachment member and wherein the second transfer member is engageable with the attachment member in a manner which prevents the relative rotation of the second transfer member and the attachment member. The second transfer member and the attachment member may include a plurality of interfitting projections and recesses wherein the engagement of the projections and recesses prevents the relative rotation of the second transfer member and the attachment member.

The invention comprises, in yet another form thereof, an instrumentation guide having a guide body with at least one alignment feature. An attachment member is also provided and an orthopedic device is attachable to the attachment member. The attachment member is, when the orthopedic device is not attached thereto, detachably securable to the guide body and relatively rotatable to the guide body when detachably secured thereto. Attachment of the orthopedic device to the attachment member secures the orthopedic device in a predetermined position relative to the instrumentation guide.

The attachment member may comprise a shaft having a threaded end. The guide body may also include a passageway having a threaded portion which is threadingly engageable with the threaded end and wherein the attachment member is detachably securable to the guide body by threading the threaded end through the threaded portion.

A transfer member having first and second ends may also be provided. The first end of the transfer member is both engageable and disengagable with the attachment member while the orthopedic device is attached to the attachment member. A force receiving member is disposed on the transfer member proximate the second end of the transfer member.

The invention comprises, in an additional form thereof, an instrumentation guide having a guide body with at least one alignment feature. An attachment member is secured to the guide body. An orthopedic device is attachable to the attachment member in a predetermined position relative to the instrumentation guide. A transfer member having a non-threaded quick connect mechanism is provided. The quick connect mechanism secures the transfer member in a fixed relative position to the instrumentation guide and is both engageable and disengageable with the instrumentation guide when the orthopedic device is attached to the attachment member. A force receiving member is disposed on the transfer member.

The guide body may also include a cavity with the quick release mechanism being disposed within the cavity when engaged with the instrumentation guide.

The guide body may also be substantially radio-transparent and the transfer member may be substantially metallic.

An advantage of the present invention is that a transfer member which is easily removable from the instrumentation guide without requiring detachment of the nail from the instrumentation guide, may be manufactured of a radio opaque material such as metal and be removed from the guide when obtaining radiographic images, such as X-ray images, to prevent the transfer member from obscuring the radiographic images.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 1 is a partial perspective view of an instrumentation guide in accordance with the present invention.

FIG. 2 is a sectional perspective view of the instrumentation guide.

FIG. 3 is a sectional view of the instrumentation guide.

FIG. 4 is a sectional perspective partial view of the instrumentation guide and showing the attachment member.

FIG. 7 is a partially cross sectional and exploded view of a second embodiment of the invention.

Corresponding reference characters indicate corresponding parts throughout the several views. The embodiment described below is set out as an exemplification of the invention and is not intended to be exhaustive or to be construed as limiting the scope of the invention to the precise form disclosed.

DESCRIPTION OF THE PRESENT INVENTION

Figures 5, 6:
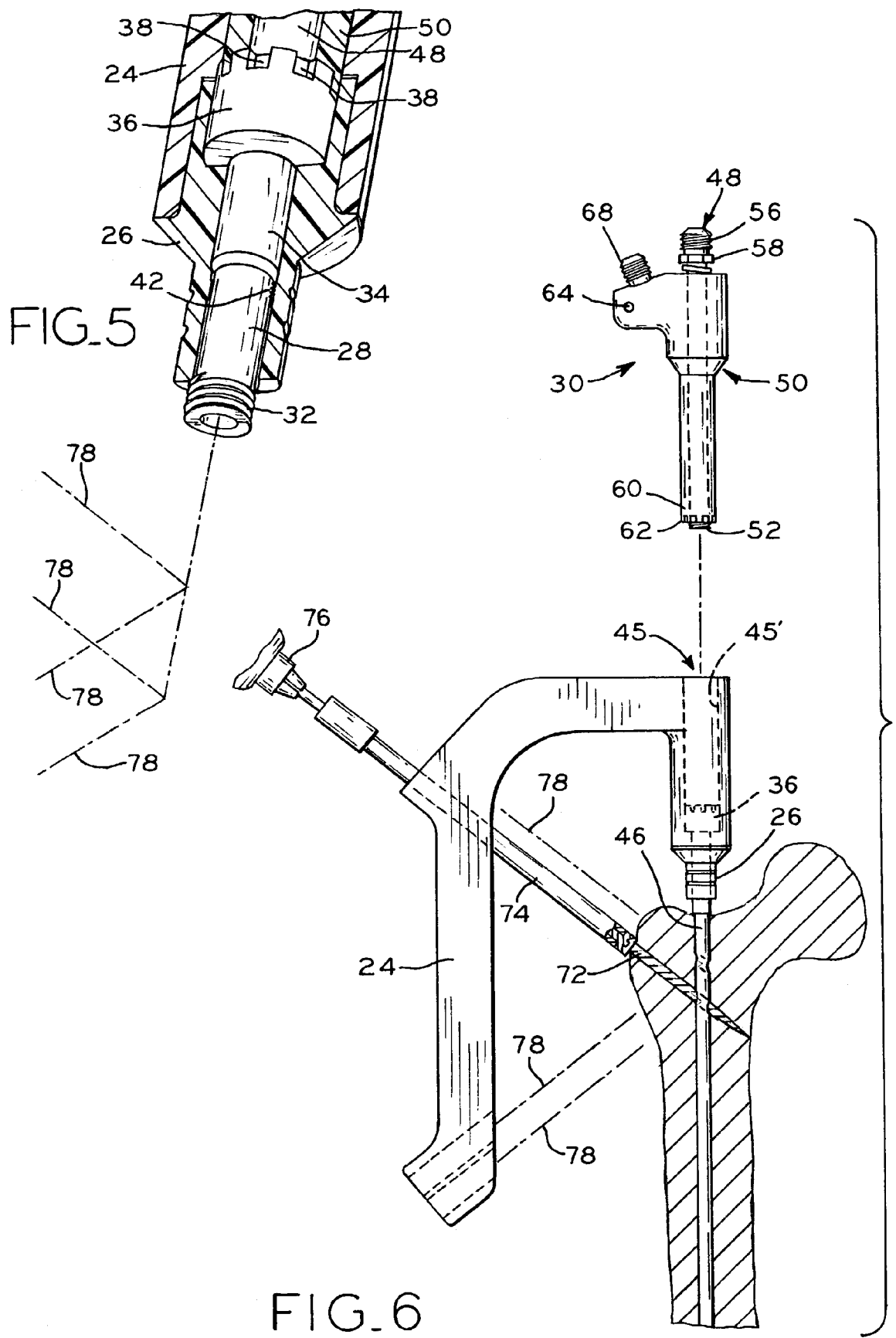
FIG. 5 is another sectional perspective partial view of the instrumentation guide showing the attachment member.
FIG. 6 is an exploded view of the instrumentation guide.

An instrumentation guide 20 in accordance with the present invention is shown in FIG. 1. The instrumentation guide 20 includes a guide body 22 which, in the embodiment of FIGS. 1–6, has a two piece construction with the two portions forming the guide body being a handle portion 24 and an insert 26. Handle portion 24 is formed out of a radio transparent material. Radio transparent materials which may be used to form handle portion 24 are well known in the art and one example of such a material is a composite material of poly ether ether ketone (PEEK) and carbon fibers such as that available from Greene, Tweed & Co. under the mark Orthtek. Insert 26 is formed of a metallic material which, in the illustrated embodiment is a stainless steel.

Instrumentation guide 20 also includes an attachment member 28 and transfer member 30 which are both removable from the instrumentation guide 20. In the disclosed embodiment, both attachment member 28 and transfer member 30 are formed of stainless steel. Attachment member 28 includes external threads 32 disposed near one end of a shaft 34. An enlarged generally cylindrical head 36 is located on shaft 34 opposite threads 32. Threads 32 are used to engage the internal threads of an intramedullary rod or nail and thereby secure the rod or nail to instrumentation guide 20 as explained in greater detail below. Head 36 includes a plurality of recesses or keyways 38 located circumferentially about its upper surface. The illustrated embodiment includes eight recesses 38 and an internally threaded opening 40 which are also discussed in greater detail below.

Attachment member 28 is removably captured in instrumentation guide 20 by insert 26. As can be seen in FIG. 4, insert 26 has a passageway 27 or bore hole taking the form of a cylindrical opening extending therethrough. Attachment member 28 extends through the bore hole. The interior surface of the bore hole through insert 26 includes a threaded portion defined by threads 42 which are sized to cooperate with threads 32 located on attachment member 28. Referring to FIG. 6, attachment member 28 is secured to instrumentation guide 20 by inserting attachment member 28 through opening 45' of handle portion 24. Threads 32 are then turned through threads 42 to allow threads 32 and a portion of shaft 34 to pass through threads 42. As can be seen in FIG. 4, after threads 32 have been passed through threads 42, a non-threaded portion of shaft 34 is located within threads 42.

Once threads 32 have been turned through threads 42 on the interior of insert 26, interference between head 36 and insert 26 requires that threads 32 be turned through threads 42 once again in the opposite direction to remove attachment member 28 from insert 26. The use of threads 42 in cooperation with threads 32 thereby "captures" attachment member 28 by requiring the relatively involved action of unthreading attachment member 28 to remove member 28 from instrumentation guide 20 and thereby inhibiting the inadvertent removal of attachment member 28 from instrumentation guide 20. For example, once attachment member 28 has been installed by turning threads 32 through threads 42, attachment member 28 will not inadvertently fall to the floor merely because the instrumentation guide is held at a particular orientation. This method of installing attachment member 28 on instrumentation guide 20, while inhibiting the accidental removal of attachment member 28, also allows for the relatively easy removal of attachment member 28 from the instrumentation guide 20 to thereby facilitate the disassembly and cleaning of instrumentation guide 20.

After installation within guide body 22, attachment member 28 includes a first portion, i.e., threaded end 32, which projects outwardly therefrom for engagement with an intramedullary nail and a second portion, i.e., enlarged cylindrical head 36, which is located in cavity 45' of guide body 22 and is engageable with transfer member assemblage 30 as discussed below.

Shaft 34 and head 36 are sized to permit their rotation within insert 26 after attachment member 28 has been installed within instrumentation guide 20. Insert 26 includes projections 44 which are configured to interfit with recesses on the end of an intramedullary nail 46. Intramedullary rods or nails 46 typically have one end which defines an internally threaded bore and has notches located in the rim of the bore to facilitate the rotational fixation of the nail while a threaded member is engaged with the internally threaded bore of the nail. Intramedullary rods or nails 46 are secured to the instrumentation guide 20 by aligning and interfitting the notches located at one end of the nail or rod with projections 44 and then engaging threads 32 with the internally threaded bore of the nail until the nail is held firmly against insert 26 and thereby fixes the nail in a predetermined position with respect to guide body 22.

Attachment member 28 is rotated with respect to guide body 22 by a T-handled driver (not shown) having an end which is inserted through opening 45 into cavity 45' defined by guide body 22. The inserted end of the T-handled driver includes projections which matingly engage the recesses 38 of attachment member 28 for drivingly rotating member 28 while the guide body 22 is held stationary. After the nail 46 or rod is secured to instrumentation guide 20, the transfer member 30 is attached.

The illustrated embodiment includes a transfer member 30 which takes the form of a transfer member assemblage having a first transfer member 48 and a second transfer member 50. The illustrated embodiment has a first transfer member formed by an inner elongate member or shaft 48 and the second transfer member is an outer body which forms a sleeve 50 within which shaft 48 is located. Both shaft 48 and outer sleeve 50 are formed out of stainless steel in the illustrated embodiment. Shaft 48 includes a first threaded end 52 which engages the internally threaded opening 40 located on attachment member 28. A shaft portion 54 connects first end 52 with a second threaded end 56 of shaft 48. Also located at the second end of shaft 48 is an integral bolt head 58. Bolt head 58 is used to engage inner shaft 48 with attachment member 28 and thereby secure transfer member 30 to the instrumentation guide in a fixed position relative to the attachment member as described in greater detail below.

Inner shaft 48 is removably inserted into outer sleeve 50 and may be rotated with respect to sleeve 50. A first end 60 of sleeve 50 has a plurality of projections 62 which matingly engage with recesses 38 located on attachment member 28. Although the illustrated embodiment employs a plurality of projections and recesses located on the attachment member 28 and on sleeve 50, alternative methods of rotationally securing these two components may also be employed. The first end of transfer member 30 is inserted through opening 45 into cavity 45' when engaging the first end of the transfer member assemblage 30 with attachment member 28. To securely engage inner shaft 48 to attachment member 28, first end 60 of sleeve 50 and its projections 62 are engaged with recesses 38 located on attachment member 28 to rotationally secure sleeve 50 with member 28, i.e., prevent relative rotational movement between sleeve 50 and member 28. Then, inner shaft 48 is rotated relative to both outer sleeve 50 and attachment member 28 to threadingly engage threads 52 of shaft 48 with threaded opening 40 of attachment member 28. Bolt head 58 located on inner shaft 48 provides a mechanism for gripping and rotating shaft 48 whereas opening 64 located on sleeve 50 provides a mechanism for engaging sleeve 50 to thereby relatively rotate shaft 48 with respect to sleeve 50 and attachment member 28 which is rotationally engaged with sleeve 50.

As can be seen in FIG. 2, a substantial portion of transfer member 30 is located within cavity 45' when transfer member 30 is engaged with attachment member 28. Transfer member 30 may be engaged and disengaged with the attachment member 28 as discussed above while a nail 46 remains attached to the opposite side of the attachment member 28. This enables the transfer member 30, which may be substantially metallic, to be removed from guide body 22 during a surgical procedure. This ability to remove the transfer member 30 facilitates the taking of radiographic images while the guide body 22, which is substantially radio-transparent, remains firmly secured to a nail 46 in a predetermined position relative thereto after the nail has been inserted into an intramedullary canal. If necessary, the transfer member 30 can be re-engaged with the attachment member 28 with the nail 46 still attached to the opposite side of attachment member 28.

After nail 46 and transfer member 30 have been attached to attachment member 28, force may be applied to transfer member 30 to insert or remove nail 46 from an intramedullary canal. To facilitate delivery of forces to a nail 46 or intramedullary rod secured to attachment member 28, inner shaft 48 includes a force receiving member which takes the form of a threaded projection 56. To insert nail 46, a mushroom headed cap 66 having an internally threaded opening can be attached to threaded projection 56 as shown in FIG. 3. Cap 66 can then be struck with a hammer, not shown, to drive nail 46 into an intramedullary canal. By utilizing a removable cap 66 with inner shaft 48, the wear caused by the direct impact of the hammer is primarily located on cap 66 which may be more cost effectively replaced than inner shaft 48. Alternatively, a slap hammer, not shown, can be threadingly attached to threaded projection 56 to impart insertion or removal forces to attached nail 46. Slap hammers are well known in the art and typically have a weight with a grip mounted on a shaft whereby the weight may be slid along the shaft to impart a driving force upon impact in either direction.

Outer sleeve 50 includes a threaded projection 68 which is similar to threaded projection 56 such that either cap 66 or a slap hammer may be attached to projection 68. The two force receiving members shown in the embodiment of FIGS. 1–6, i.e., threaded projections 56 and 68, are positioned to form an angle therebetween and both are positioned proximate the second end of transfer member 30 opposite attachment member 28. Projection 68, which is positioned at an angle to inner shaft 48, is useful for some patients, such as obese patients, where the position of projection 68 provides access to transfer member 30 when access to threaded end 56 may be wholly or partially obstructed. Similar to threaded end 56, threaded projection 68 facilitates the delivery of both insertion and removal forces.

Insertion and removal forces imparted to inner shaft 48 through threaded end 56 are transferred to attachment member 28 through the engagement of threads 52 and threaded opening 40. Insertion forces imparted to projection 68 are transferred to attachment member 28 by end 60 of sleeve 50 bearing against head 36 of attachment member 28 while the removal forces imparted to projection 68 are transferred to attachment member 28 by engagement of sleeve 50 with bolt head 58, either directly or through an intermediate washer, inner shaft 48 then transfers the removal forces to attachment member 28 via threads 52.

The forces imparted to attachment member 28 from projection 68 have a component force which is directed along the axis defined by shaft 54 and a transverse force perpendicular to shaft 54. By positioning projection 68 in alignment with guide body 24, the outer portion of guide body 24 can be gripped to counteract the forces imparted by projection 68 which are transverse to shaft 54.

Although instrumentation guide 20 illustrated in FIGS. 1–6 includes a transfer member 30 which directly engages and directly transmits forces to attachment member 28, transfer member 30 of instrumentation guide 20 could alternatively engage a different component of instrumentation guide 20 provided that the insertion and removal forces conveyed by transfer member 30 were transferred through intermediate parts to attachment member 28.

As best seen in FIGS. 3 and 6, guide body 22 includes alignment features 70 which, in the illustrated embodiment, take the form of bore holes. Since nail 46 is securable to guide body 22 in a predetermined position relative to the guide body 22, alignment features 70 can be positioned to align with transverse openings in the nail 46 to facilitate the insertion of screws 72 therethrough in a manner well known in the art. Dashed lines 78 illustrate how alignment features 70 provide a reference axis for use when installing a screw 72 in a transverse opening in a nail 46. As can be seen in FIG. 6, instrumentation, including a bushing 74 and drill 76 may be used to install screws 72.

During the installation of such screws 72 it may be desirable to take radiographic images. By removing transfer member 30 during the taking of such radiographic images, the metallic transfer member 30 will not obscure the acquired images. It is advantageous to use a relatively strong material, such as a stainless steel or other metallic material, to form member 30 which transfers the insertion and removal forces to nail 46. Although illustrated guide body 22 is substantially radio-transparent, insert 26 is metallic. By limiting metallic insert 26 to the area proximate attachment member 28, the obscuration of the radiographic images by insert 26 can also be limited while enabling such details as threads 42 to be formed out of a metallic material.

An alternative embodiment of the present invention is shown in FIG. 7. The embodiment shown in FIG. 7 includes a transfer member 80 having a non-threaded quick connect mechanism 82 which secures transfer member 80 to guide body 90 in a fixed relative position to attachment member 100. As discussed in greater detail below, the quick connect mechanism 82 is both engageable and disengageable with the instrumentation guide when an orthopedic device, such as an intramedullary nail 46 or rod, is attached to attachment member 100.

The quick connect mechanism 82 includes a plurality of spherical bearings 84 which project through openings in the transfer member 80 and are biased outwardly by a downwardly biased plunger 86. A biasing element 88 is schematically illustrated in FIG. 7 and is used to bias the plunger 86 downward. Biasing element 88 may include a spring to provide a biasing force. A release mechanism (not shown) may be located on the transfer member 80 to facilitate the disengagement of quick connect mechanism 82. If the biasing force exerted on plunger 86 is not excessive, a release mechanism may not be required.

A projection 89 is located on the bottom of transfer member 80 and is engageable with the recess 102 located on head 104 of attachment member 100.

Guide body 90 includes a first portion 92 which is a radio-transparent body having alignment features similar to handle portion 24, and a second portion 94 which is a metallic insert member. Insert member 94 may advantageously include a knurled surface where it engages first portion 92. Guide body 90 also defines a cavity 96 which takes the form of a cylindrical bore and receives the end of transfer member 80.

Insert 94 includes a groove 98 which receives bearings 84 to thereby engage guide body 90 with transfer member 80 through quick connect mechanism 82. Alternative shapes of grooves and bearings may also be employed with quick connect mechanism 82. Alternative forms of known quick connect mechanisms may also be employed with transfer member 80. Insert 94 also includes a passageway 106 which includes threads 108 which function similar to threads 42. Insert 94 also includes projections 110 which interfit with an attached nail 46 similar to projections 44 discussed above.

Typically, intramedullary nails are handed, i.e., designed for use on the left or right side of a patient such as in the left or right femur. Such nails often have differently configured notches and may require the use of two different instrumentation guides having differently configured projections 44 or 110. It is envisioned that mounting projections 110 in a manner which permits their rotation by 180 degrees relative to insert 94 would allow the same guide body 90 to be used with both "left" and "right" nails 46.

Attachment member 100 includes a threaded end 112 and shaft 114 which are similar to threaded end 32 and shaft 34 of attachment member 28. Head 104 includes a recess 102 which has a lower portion which is engageable by a hex head driver (not shown) to secure threaded end 112 to a nail 46 or similar orthopedic device.

Projection 89 is seated within the upper portion of recess 102 when quick connect mechanism 82 is engaged with insert 94. Lower surface 87 of transfer member 80 bears against the upper surface 105 of head 104 to impart insertion forces to attachment member 100. Transfer member 80 includes a force receiving member 116 at its end opposite projection 89. Member 116 is a threaded projection which functions similar to threaded projections 56 and 68. Alternative force receiving members could also be employed. Although illustrated transfer member 80 takes the form of a straight elongate member, using a pivot mechanism with transfer member 80 would allow force receiving member 116 to be placed at a variety of different positions relative to projection 89.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains. Accordingly, the scope of the invention should be determined not by the illustrated embodiments but by the following claims and their legal equivalents.

What is claimed is:

1. An instrumentation guide for an orthopedic device and instruments associated therewith, said instrumentation guide comprising:

a guide body, said guide body defining a cavity and having at least one alignment feature;

an attachment member secured to said guide body, the orthopedic device being attachable to said attachment member in a predetermined position relative to said instrumentation guide; and a transfer member having first and second ends, said first end being insertable into said cavity and wherein said transfer member is engageable with said attachment member to secure said transfer member in a fixed position relative to said attachment member and wherein said transfer member is both engageable and disengageable with said attachment member with the orthopedic device attached to said attachment member, said second end including a force receiving member wherein said force receiving member is positioned outside said cavity when said transfer member is engaged with said instrumentation guide;

wherein said attachment member includes a first portion and a second portion, the orthopedic device being attachable to said first portion and said second portion being disposed in said cavity and wherein said transfer member is secured in said fixed position by engagement of said first end of said transfer member with said second portion of said attachment member, wherein said first member comprises an inner shaft and said second member comprises an outer sleeve, said force receiving member being disposed on said first member.

2. The instrumentation guide of claim 1 wherein said force receiving member comprises a threaded projection.

3. The instrumentation guide of claim 1 wherein said guide body is substantially radio-transparent.

4. The instrumentation guide of claim 3 wherein said guide body comprises a first guide body portion and a second guide body portion, said first guide body portion being radio-transparent, said second guide body portion being a metallic portion securable to said attachment member.

5. The instrumentation guide of claim 1 wherein a substantial portion of said transfer member is positioned within said cavity when said transfer member is engaged with said instrumentation guide.

6. The instrumentation guide of claim 1 wherein said transfer member further comprises a second force receiving member.

7. The instrumentation guide of claim 6 wherein said force receiving members each comprise a threaded projection and said threaded projections define an angle therebetween.

8. The instrumentation guide of claim 1 wherein said transfer member comprises relatively rotatable first and second members, engagement of said first end of said transfer member with said attachment member comprising relative rotational movement between said first and second members.

9. The instrumentation guide of claim 1, wherein said first end of said transfer member includes a non-threaded quick connect mechanism for securing said transfer member in a fixed relative position to said attachment member, said mechanism being both engageable and disengageable with attachment member when the orthopedic device is attached to said attachment member.

10. An instrumentation guide for an orthopedic device and instruments associated therewith, said instrumentation guide comprising:
a guide body, said guide body having at least one alignment feature;
an attachment member secured to said guide body and wherein the orthopedic device is attachable to said attachment member in a predetermined position relative to said instrumentation guide;
a transfer member assemblage having first and second ends, said first end being both engageable and disengageable with said attachment member when the orthopedic device is attached to said attachment member, said transfer member assemblage including relatively rotatable first and second transfer members, engagement of said first end of said transfer member assemblage with said attachment member comprising relative rotational movement between said first and second transfer members; and
a force receiving member disposed on said transfer member assemblage proximate said second end;
wherein said second transfer member and said attachment member include a plurality of interfitting projections and recesses, engagement of said projections and recesses preventing relative rotation of said second transfer member and said attachment member.

11. The instrumentation guide of claim 10 wherein both said first transfer member and said second transfer member are engageable with said attachment member, said first transfer member comprising an elongate shaft having a threaded end engageable with said attachment member and engagement of said second transfer member with said attachment member preventing relative rotation therebetween.

12. The instrumentation guide of claim 11 wherein said force receiving member comprises a first threaded projection disposed opposite said threaded end of said first transfer member and said second transfer member includes a second force receiving member comprising a second threaded projection, said first and second threaded projections defining an angle therebetween.

13. The instrumentation guide of claim 10 wherein said guide body is substantially radio-transparent and said transfer member assemblage is substantially metallic.

14. An instrumentation guide for an orthopedic device and instruments associated therewith, said instrumentation guide comprising:
a guide body, said guide body having at least one alignment feature;
an attachment member including a shaft having threaded end engageable with the orthopedic device and an enlarged head disposed opposite said threaded end, the orthopedic device being attachable to said attachment member; wherein, without the orthopedic device attached thereto, said attachment member is detachably securable to said guide body and relatively rotatable to said guide body when detachably secured thereto; and wherein attachment of the orthopedic device to said attachment member secures the orthopedic device in a predetermined position relative to said instrumentation guide;
a transfer member assemblage having first and second ends, said first end being both engageable and disengageable with said enlarged head of said attachment member when the orthopedic device is attached to said attachment member, said transfer member assemblage including relatively rotatable first and second transfer members, engagement of said first end of said transfer member assemblage with said attachment member comprising relative rotational movement between said first and second transfer members; and
a force receiving member disposed on said transfer member assemblage proximate said second end,
wherein said attachment member comprises a shaft having a threaded end, and said guide body defines a passageway having a threaded portion threadingly engageable with said threaded end, said attachment member being detachably securable to said guide body by threading said threaded end through said threaded portion.

15. The instrumentation guide of claim 14 wherein said first transfer member is threadingly engageable with said attachment member and wherein said second transfer member and said attachment member further comprise a plurality of interfitting projections and recesses, engagement of said projections and recesses preventing relative rotation of said second transfer member and said attachment member.

16. The instrumentation guide of claim 14 wherein said transfer member comprises a second force receiving member.

17. An instrumentation guide for implanting an orthopedic device, the instrumentation guide comprising:
an attachment assembly including a guide body and an attachment member, said guide body having a cavity extending between an insert end and a transfer end, said attachment member extending into said cavity at said insert end, said attachment member having an attachment end disposed within said cavity and an opposing engagement end adapted to couple with the device; and
a transfer member having first and second ends, said first end extending into said cavity at said transfer end, said first end releasably engaged with said attachment end of said attachment member such that said transfer member is releasably secured to said attachment assembly in a fixed position relative to said attachment member, said second end including a force receiving member positioned outside said transfer end of said cavity, wherein said transfer member is releasable from said attachment assembly while said attachment member is coupled with the device, wherein said transfer member comprises a second force receiving member and each of said force receiving members comprises a threaded projection and said threaded projections define an angle therebetween.

18. The instrument guide of claim 17 wherein each of said first end and said attachment end include a plurality of complementary projections and recesses, engagement of said projections and recesses of said first end with said projections and recesses of said attachment end preventing rotation of said first transfer member relative to said attachment member.

19. The instrument guide of claim 17 wherein said transfer member includes first and second transfer members, said first and second transfer members being rotatable relative to one another, both said first transfer member and said second transfer member releasably engaged with said attachment member, said first transfer member comprising an elongate shaft having a threaded end configured to engage with a threaded opening in said attachment end of said attachment member and said second transfer member comprising an outer sleeve, said shaft extending through said outer sleeve, said second transfer member releasably engaged with said attachment end of said attachment member to thereby prevent relative rotation between said second transfer member and said attachment member.

20. An instrumentation guide for an orthopedic device and instruments associated therewith, said instrumentation guide comprising:
   a guide body, said guide body having at least one alignment feature;
   an attachment member, the orthopedic device being attachable to said attachment member; wherein, without the orthopedic device attached thereto, said attachment member is detachably securable to said guide body and relatively rotatable to said guide body when detachably secured thereto; and wherein attachment of the orthopedic device to said attachment member secures the orthopedic device in a predetermined position relative to said instrumentation guide; and
   a transfer member having a non-threaded quick connect mechanism for securing said transfer member to said attachment member, said transfer member being both engageable and disengageable when the orthopedic device is attached to said attachment member
   wherein said attachment member comprises a shaft having a threaded end, and said guide body defines a passageway having a threaded portion threadingly engageable with said threaded end, said attachment member being detachably securable to said guide body by threading said threaded end through said threaded portion.

* * * * *